United States Patent
O'Driscoll et al.

(10) Patent No.: US 9,981,063 B2
(45) Date of Patent: May 29, 2018

(54) BIOSYNTHETIC COMPOSITE FOR OSTEOCHONDRAL DEFECT REPAIR

(75) Inventors: Shawn W. O'Driscoll, Rochester, MN (US); David G. Lewallen, Rochester, MN (US); Rodrigo Mardones, Santiago (CL)

(73) Assignee: Mayo Foundation for Medical Education and Research, Rochester, MN (US)

( * ) Notice: Subject to any disclaimer, the term of this patent is extended or adjusted under 35 U.S.C. 154(b) by 2209 days.

(21) Appl. No.: 11/286,593

(22) Filed: Nov. 23, 2005

(65) Prior Publication Data

US 2006/0195188 A1 Aug. 31, 2006

Related U.S. Application Data

(60) Provisional application No. 60/630,622, filed on Nov. 24, 2004.

(51) Int. Cl.
| | |
|---|---|
| *A61F 2/28* | (2006.01) |
| *A61L 27/36* | (2006.01) |
| *A61F 2/30* | (2006.01) |
| *A61L 27/42* | (2006.01) |
| *A61L 27/56* | (2006.01) |
| *A61F 2/46* | (2006.01) |

(52) U.S. Cl.
CPC ...... *A61L 27/3683* (2013.01); *A61F 2/30756* (2013.01); *A61L 27/3604* (2013.01); *A61L 27/365* (2013.01); *A61L 27/3654* (2013.01); *A61L 27/427* (2013.01); *A61L 27/56* (2013.01); *A61F 2/468* (2013.01); *A61F 2002/2817* (2013.01); *A61F 2002/30764* (2013.01); *A61F 2002/30766* (2013.01); *A61F 2310/00131* (2013.01); *A61F 2310/00365* (2013.01)

(58) Field of Classification Search
CPC .................................. A61F 2/28; C12N 5/08
USPC ...... 623/14.12, 23.5, 23.54, 23.55, 623/23.57–23.61, 23.63
See application file for complete search history.

(56) References Cited

U.S. PATENT DOCUMENTS

| | | |
|---|---|---|
| 4,846,835 A | 7/1989 | Grande |
| 5,041,138 A | 8/1991 | Vacanti et al. |
| 5,282,861 A | 2/1994 | Kaplan |

(Continued)

OTHER PUBLICATIONS

Freed et al., "Joint resurfacing using allograft chondrocytes and synthetic biodegradable polymer scaffolds", Journal of Biomedical Materials Research, vol. 28, 891-899, 1994.

*Primary Examiner* — Yashita Sharma
(74) *Attorney, Agent, or Firm* — Quarles & Brady LLP (57) ABSTRACT

A composite for osteochondral defect repair includes a porous scaffold and a periosteal graft secured to a surface of the scaffold. The composite provides cartilage growth from autologous periosteum chondrogenesis. Biological resurfacing of large osteochondral defects, or a complete joint is feasible using the porous scaffold/autologous periosteal composite. The use of this composite eliminates the necessity of using normal cartilage surface as a donor site and its respective associated morbidity. In one form, the strong bone integration capacity of a porous metal (e.g., tantalum) scaffold and the high grade of integration observed from periosteal chondrogenesis into the normal cartilage eliminates the lack of chondral-chondral integration observed in the autologous osteochondral graft technique.

4 Claims, 7 Drawing Sheets

(56) References Cited

U.S. PATENT DOCUMENTS

| | | |
|---|---|---|
| 5,700,289 A | 12/1997 | Breitbart et al. |
| 5,842,477 A * | 12/1998 | Naughton ............ A61F 2/30756 |
| | | 128/898 |
| 6,582,960 B1 | 6/2003 | Martin et al. |
| 2003/0050709 A1 | 3/2003 | Noth et al. |
| 2003/0220696 A1* | 11/2003 | Levine et al. ............. 623/17.17 |
| 2003/0229400 A1 | 12/2003 | Masuda et al. |
| 2004/0078090 A1 | 4/2004 | Binette et al. |
| 2005/0209705 A1* | 9/2005 | Niederauer et al. ....... 623/23.63 |

* cited by examiner

BIOSYNTHETIC COMPOSITE FOR OSTEOCHONDRAL DEFECT REPAIR

CROSS-REFERENCES TO RELATED APPLICATIONS

This application claims priority from U.S. Provisional Patent Application No. 60/630,622 filed Nov. 24, 2004.

STATEMENT REGARDING FEDERALLY SPONSORED RESEARCH

Not Applicable.

BACKGROUND OF THE INVENTION

1. Field of the Invention

This invention relates to an improved method and new devices for the treatment of osteochondral defects. More particularly, the invention relates to a biosynthetic composite for osteochondral defect repair.

2. Description of the Related Art

Articular cartilage is the remarkably durable tissue that covers the articulating bone surfaces in our joints and permits pain-free movement by greatly reducing friction between bones and distributing stress. Damaged cartilage is a frequent problem in our population. Unfortunately, damaged articular cartilage has a limited ability to heal and can lead to premature arthritis.

Adult articular cartilage contains no blood supply, neural network or lymphatic drainage. As a result, partial thickness defects that do not reach the subchondral bone stimulate only a transient induction of chondrocyte replication and matrix production in the area adjacent to the wound. In young patients with focal and small lesions reparative/regenerative alternatives have been used with acceptable results as well as biological resurfacing in selected cases. Nevertheless, when a young patient presents with a large focal osteochondral defect due to trauma or avascular necrosis, and the defect of both bone and cartilage are too large to accept any regenerative procedure, there are currently no clinically proven treatment options.

Clinicians and researchers have been striving to develop methods of articular cartilage repair based on experimental studies showing the potential for cartilage repair through the use of transplanted chondrocytes, mesenchymal stem cells, or undifferentiated tissues containing stem cells or chondrocyte precursors (such as periosteum or perichondrium). In addition, periosteum tissue regenerates both cartilage and bone, and has been used successfully in biological resurfacing for the repair of damaged articular cartilage.

Currently, there are two general approaches to cartilage repair: (1) insertion of a new fragment of cartilage that has been generated in vitro, or (2) repair or regeneration of new cartilage in situ. The latter can be attempted either (a) by recruiting and inducing local cells with bioactive agents (growth factors) or (b) by implanting cells or tissue with the potential to form a new cartilage surface. Cells can be transplanted in a matrix such as an absorbable polymer or a suspension that is held in place with a cover. Cell transplantation can be performed using either undifferentiated chondrocyte precursor cells from periosteum, mesenchymal stem cells from bone marrow, or chondrocytes. Another approach is to transplant a tissue with chondrogenic potential, such as periosteum or perichondrium.

Attempts have been made to enhance the intrinsic potential of cartilage for self-repair using continuous passive motion, electricity, implanting scaffolds for repair and growth factors. Continuous passive motion is helpful for small defects, less than 3 millimeters in diameter, and electricity has not been proven to induce cartilage healing. Implanted scaffolds such as carbon fiber promote healing with fibrous tissue but not with cartilage. The local application of growth factors is very promising as a means of inducing local cells from the marrow and/or adjacent cartilage to participate in the repair process. Problems associated with intra-articular use of growth factors such as TGF-β include the undesirable side effects such as development of osteophytes. The potential benefit of enzymatic preparation of the defect surfaces in cartilage repair has also been demonstrated.

Figure 1:
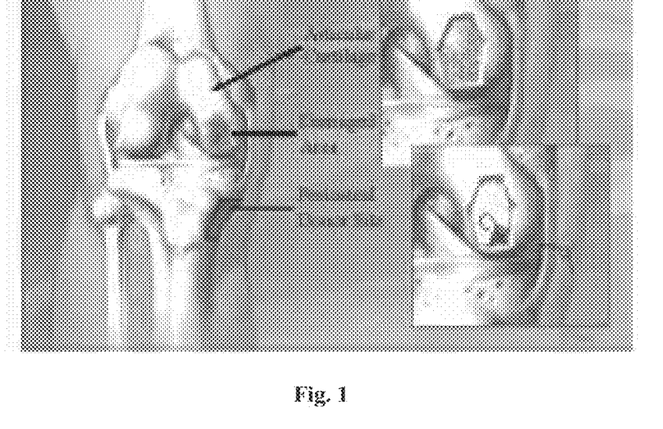
FIG. 1 is a depiction showing how cartilage repair is possible with periosteal grafts. Periosteum from the proximal medial tibia is sutured into the defect after debridement of the lesion down to the subchondral bone. The top reference line is articular cartilage; the middle reference line is the damaged area; and the bottom reference line is the periosteal donor site.
Figure 2:
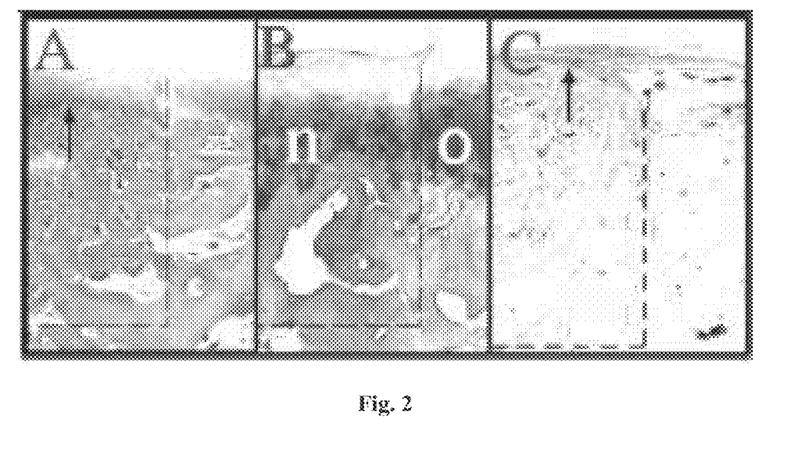
FIG. 2 includes photographs showing that regenerated cartilage from periosteal grafts demonstrates acceptable long-term durability.

Periosteal grafts have been shown to have the potential for neochondrogenesis and can be used to repair articular cartilage defects in experimental animals (see FIG. 1 in which periosteum from the proximal medial tibia is sutured into a damaged area after debridement of the lesion down to the subchondral bone). The regenerated cartilage demonstrates acceptable long-term durability (see FIG. 2B). This new tissue has histological, histochemical and biochemical characteristics that are similar to those of normal articular cartilage. Although periosteum has the potential to produce bone via either endochondral or intramembranous ossification, periosteal neocartilage does not all calcify or ossify. In vivo studies show that newly formed cartilage from periosteum in osteoarticular defects in rabbits remained free of calcification at long-term follow-up (1 year in rabbits—see FIG. 2B). Endochondral replacement of the new cartilage did occur in the subchondral region originally occupied by bone. This process continued up to the level of the normal cartilage-bone junction (the tidemark), which was evident by the fourth week (see FIG. 2A), and remained stable for 1 year following surgery. Furthermore, the repair cartilage retained the appearance of hyaline articular cartilage, not epiphyseal cartilage, and did not show signs of hypertrophy. Thus, periosteal neocartilage is not predestined to either terminal hypertrophy or calcification. Calcification and/or ossification of cartilage appears to be regulated separately from chondrogenesis itself. Mechanical factors are important, because if the newly formed cartilage does not articulate with an opposing surface, such as occurs when the patella dislocates, the new tissue does ossify (see FIG. 2C).

In the treatment of full-thickness cartilage defects, there are several surgical resurfacing options available. The clinical outcomes of these procedures remain controversial. For example, debridement, subchondral penetration and abrasion arthroplasty are limited to the treatment of small lesions ($<2$ cm$^2$) and result in a fibrous repair tissue with poor biomechanical properties.

Autologous chondrocyte transplantation and autologous osteochondral transplantation are probably the most extensively used alternative approaches for resurfacing lesions larger than 2 cm$^2$ ($<10$ cm$^2$). Autologous chondrocyte transplantation is a biological repair technique that has produced effective repair tissue in particular locations. However, the long-term viability of the hyaline-like repair tissue has not been proven. The viability of the transplanted cells has also been questioned. In addition, recent results have been reported that indicate that autologous chondrocyte transplantation is no better then either autologous osteochondral cylinder transplantation or microfracture techniques.

In the case of autologous osteochondral grafts, it has been shown in animal studies that the cartilage surface retains its structural and biochemical integrity. Additionally, clinical reports have demonstrated that when a well-standardized technique is performed and when indications are strictly followed, the results are promising and reproducible. However, there is still great concern regarding the donor site morbidity with 50-80% of patients reporting symptoms attributable to the donor site. Furthermore, progressive deterioration of the cartilage surrounding the donor site and involving weight bearing surface areas remains a main concern with this technique.

Thus, the development of a composite with the biochemical and mechanical properties of an autologous osteochondral graft with better integration properties and without the need for osteochondral graft harvesting would be very attractive.

Figure 3:
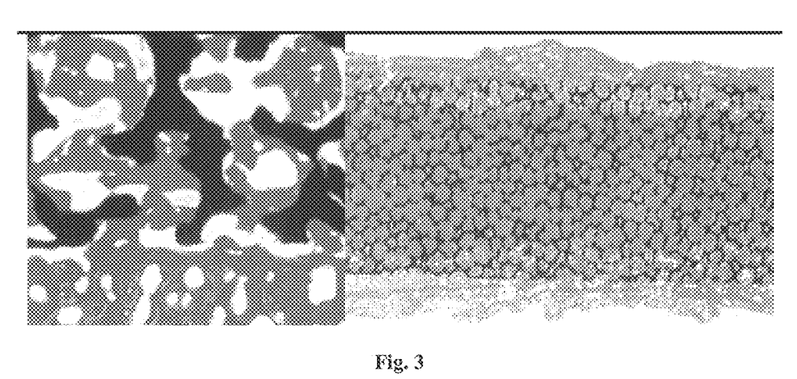
FIG. 3 includes photographs showing that the pore size and high volume porosity of trabecular metal supports vascularization and rapid secure soft tissue ingrowth. In particular, the left photograph shows bone ingrowth at 4 weeks (paragon stain, ×15) and the right photograph shows fibrous tissue ingrowth at 4 weeks (basic fuschin stain).

Open cell tantalum structures have been developed for potential application in reconstructive orthopedics and other surgical disciplines (see, e.g., U.S. Pat. No. 5,282,861). The material has high and interconnected porosity with a very regular pore sharp and size. It can be made into complex shapes and used either as a bulk implant or as a surface coating. "Trabecular metal" has been shown to permit physiologic bone in growth and healing. In transcortical implant studies, new bone rapidly infiltrated the trabecular metal. The pore size and high volume porosity of trabecular metal supports vascularization and rapid secure soft tissue ingrowth (see FIG. 3 in which the left photograph shows bone ingrowth at 4 weeks and the right photograph shows fibrous tissue ingrowth at 4 weeks).

The mechanical properties of this material when tested as a porous scaffold had an elastic modulus (~3 GPa) and compressive strength (~50-80 MPa) in-between those of cortical (~15 GPa/130-150 MPa) and trabecular bone (~0.1 GPa/~10-50 MPa) and had an elastic modulus resembling that of subchondral bone (~2 GPa). It also had a high ductility during compressive testing and allowed plastic deformity. This "trabecular metal" has been shown to permit physiologic bone ingrowth and healing. In transcortical implant studies, new bone rapidly infiltrated and remodeled into the trabecular metal. The pore size and high volume porosity of trabecular metal also supports vascularization and rapid secures soft tissue ingrowth.

Periosteum, the connective tissue that surrounds bones, has the capacity to regenerate both cartilage and bone. This unique tissue contains two discrete layers: the inner cambium layer which is believed to contain the undifferentiated mesenchymal stem cells responsible for fracture repair and the outer fibrous layer. Periosteum has been used successfully in biological resurfacing for the repair of damaged articular cartilage. For deep osteochondral defects, a bone graft can be used to replace the damaged subchondral bone. However, potential problems with the use of bone grafts include obtaining grafts of the appropriate size and shape, graft-site morbidity, and tissue integration with the surrounding tissue.

Therefore, there is no satisfactory treatment at the present time for deep osteochondral defects. Accordingly, there is a need for an improved method and new devices for the treatment of osteochondral defects.

SUMMARY OF THE INVENTION

In the present invention, a biologic prosthetic composite including a cartilage-generating graft such as periosteum and a porous scaffold (e.g., tantalum) has been developed for the treatment of osteochondral defects. When cultured under chondrogenic conditions, periosteal explants form a robust hyaline-like cartilage outgrowth that is attached to the porous scaffold by fibrous tissue ingrowth. The mechanical properties of these composites are similar to normal osteochondral plugs after only six weeks in culture. Thus, porous scaffolds (e.g., tantalum) are compatible with the chondrogenic capacity of periosteum.

As a result, a porous scaffold (e.g., tantalum) may be used instead of a bone graft as a primary structural support and interface between a periosteal explant and the subchondral bone to from a biosynthetic composite for the repair of major osteochondral defects. One advantage over other approaches is the security of graft fixation by bonding/integration to subchondral bone. Additionally, the invention is applicable with scaffolds other than tantalum, or with other cartilage-generating sources than periosteum like mesenchymal stem cells, chondrocytes, perichondrium, or a combination of them. Finally, the scaffold and cell carriers may be loaded with different matrices to carry chemical signals and/or one or more growth factors/drug release.

Therefore, in one aspect, the invention provides a composite for the repair of osteochondral defects. The composite includes a biocompatible porous scaffold, and a cartilage-generating graft, such as a periosteal graft, secured to a surface of the scaffold. In one form, the scaffold comprises a metallic material, and the scaffold has interior open spaces defined by an interconnecting network of channels. In another form, the scaffold comprises tantalum, and the scaffold has interior open spaces defined by an interconnecting network of channels. In yet another form, the scaffold comprises (i) a substrate having interior open spaces with surfaces defined by an interconnecting network of channels and (ii) a film of metallic material deposited onto the surfaces. In still another form, the scaffold comprises (i) a substrate having interior open spaces with surfaces defined by an interconnecting network of channels and (ii) a film of tantalum deposited onto the surfaces. The scaffold may be structured such that a top of the scaffold is below a level of surrounding subchondral bone when the composite is arranged in the defect.

Preferably, the periosteal graft is autologous. The periosteal graft may be pretreated in a medium including one or more growth factors that regulate periosteal cell proliferation and/or chondrogenic differentiation before the periosteal graft is secured to the surface of the scaffold. The periosteal graft may be attached to the scaffold such as with sutures. Preferably, the periosteal graft is attached to the scaffold such that the cambium layer faces away from the defect (into the joint) when the composite is arranged in the defect.

When the composite is arranged in the defect, the scaffold integrates with surrounding bone and the periosteal graft integrates with the scaffold. In one application, the scaffold and the periosteal graft occupy less than an entire volume of the defect when the composite is arranged in the defect, and a remaining volume of the defect is subsequently filled by periosteal-derived subchondral bone and neocartilage formation.

In another aspect, the invention provides a method for making a composite for the repair of an osteochondral defect in a patient. In the method, a cartilage-generating graft, such as a periosteal graft, is secured to a surface of the scaffold. In one form, the scaffold comprises a metallic material, and the scaffold has interior open spaces defined by an interconnecting network of channels. In another form, the scaffold comprises tantalum, and the scaffold has interior open spaces defined by an interconnecting network of channels. In yet another form, the scaffold comprises (i) a substrate having interior open spaces with surfaces defined by an interconnecting network of channels and (ii) a film of metallic material deposited onto the surfaces. In still another form, the scaffold comprises (i) a substrate having interior open spaces with surfaces defined by an interconnecting network of channels and (ii) a film of tantalum deposited onto the surfaces. The scaffold may be structured such that a top of the scaffold is below a level of surrounding subchondral bone when the composite is arranged in the defect.

The step of providing the periosteal graft may include the step of harvesting periosteum from the patient to provide the periosteal graft. Optionally, the periosteal graft may be pretreated in a medium including one or more growth factors that stimulate periosteal cell proliferation and/or chondrogenic differentiation. The periosteal graft may be sutured to the scaffold. Preferably, the periosteal graft is sutured to the scaffold such that the cambium layer faces away (into the joint) from the defect when the composite is arranged in the defect. The scaffold and the periosteal graft may be structured to occupy less than an entire volume of the defect when the composite is arranged in the defect.

In yet another aspect, the invention provides a method for repairing an osteochondral defect in a patient. In the method, an osteochondral defect is located in the patient, and a biocompatible porous scaffold is placed in the defect. A cartilage-generating graft, such as a periosteal graft, is then secured to a outer surface of the scaffold before or after placing the biocompatible porous scaffold in the defect. In one form, the scaffold comprises a metallic material, and the scaffold has interior open spaces defined by an interconnecting network of channels. In another form, the scaffold comprises tantalum, and the scaffold has interior open spaces defined by an interconnecting network of channels. In yet another form, the scaffold comprises (i) a substrate having interior open spaces with surfaces defined by an interconnecting network of channels and (ii) a film of metallic material deposited onto the surfaces. In still another form, the scaffold comprises (i) a substrate having interior open spaces with surfaces defined by an interconnecting network of channels and (ii) a film of tantalum deposited onto the surfaces. The scaffold may be structured such that a top of the scaffold is below a level of surrounding subchondral bone when the composite is arranged in the defect.

The periosteal graft may be harvested periosteum from the patient. Optionally, the periosteal graft is pretreated in a medium including one or more growth factors that stimulate periosteal cell proliferation and/or chondrogenic differentiation. The periosteal graft may be sutured to the scaffold, and the periosteal graft may be sutured to the scaffold after placing the biocompatible porous scaffold in the defect. Preferably, the periosteal graft is sutured to the scaffold such that the cambium layer faces away from the defect (into the joint). Also, the scaffold and the periosteal graft are structured to occupy less than an entire volume of the defect when the composite is arranged in the defect. Optionally, the defect is debrided after being located.

Therefore, the invention provides a composite for osteochondral defect repair that allows for cartilage growth from autologous periosteum chondrogenesis. Biological resurfacing of large osteochondral defects, or a complete joint is feasible using the porous scaffold/autologous periosteum composite. The use of this composite eliminates the necessity of using normal cartilage surface as a donor site and its respective associated morbidity. In one form, the strong bone integration capacity of a porous metal (e.g., tantalum) scaffold and the high grade of integration observed from periosteal chondrogenesis into the normal cartilage eliminates the lack of chondral-chondral integration observed in the autologous osteochondral graft technique.

These and other features, aspects, and advantages of the present invention will become better understood upon consideration of the following detailed description, drawings, and appended claims.

BRIEF DESCRIPTION OF THE DRAWINGS

FIG. 2A shows an early (4 week) result of cartilage repair using periosteum where the dotted line is a defect and the arrows are subchondral bone restored by endochondral ossification. FIG. 2B shows a long term result (1 year) of articular cartilage repair by periosteal grafting showing restoration of the previous subchondral-bone junction where n is newly formed cartilage and o is original cartilage. FIG. 2C shows ineffective cartilage repair due to dislocation of the patella (stained red). Without the proper mechanical influences provided by the articulating patella, we see the defect filling with fibrous tissue and bone that has grown higher than the normal cartilage (arrow) covered by pannus.

FIG. 5A shows a composite with cambium layer facing down to the tantalum. FIG. 5B shows a composite with cambium layer facing up away from the tantalum.

In FIG. 6A, periosteal explants (3 mm in diameter) are harvested from the medial proximal tibiae of 2 two-month-old New Zealand white rabbits. In FIG. 6B, the periosteal explants are placed on the tantalum with or without suture. In FIG. 6C, the periosteum/tantalum composites are cultured for six weeks using an agarose suspension culture system.

FIG. 9A is a control explant (no tantalum). FIG. 9B is an explant from composite after removal from tantalum. Explants and periosteum/tantalum composites were cultured for six weeks in the presence of ChondroMix for the first two days and exposed to ITS+ throughout the culture period.

FIG. 10A is a composite with cambium layer facing down to the tantalum (5×). FIG. 10B is a higher magnification of inset from FIG. 10A (10×). FIG. 10C is a composite with cambium layer facing up from the tantalum (5×). FIG. 10D is a higher magnification of inset from FIG. 10C (10×). The open arrow is tantalum, and the closed arrow is tissue outgrowth.

DETAILED DESCRIPTION OF THE INVENTION

The present invention provides a composite for the repair of osteochondral defects. The composite includes a biocompatible porous scaffold and a periosteal graft secured to a surface of the scaffold. In a preferred form, the scaffold has a substrate having interior open spaces with surfaces defined by an interconnecting network of channels, and a film of tantalum is deposited onto the surfaces. One example of this type of tantalum scaffold in described in U.S. Pat. No. 5,282,861 which is incorporated herein by reference. The scaffold is structured such that the top of the scaffold is below a level of surrounding subchondral bone when the composite is arranged in the defect. As used herein, a "biocompatible" scaffold is one which stimulates only a mild, often transient, implantation response, as opposed to a severe or escalating response.

Preferably, the periosteal graft is autologous, and is pretreated in a medium including one or more growth factors, such as transforming growth factor (TGF), that stimulates periosteal cell proliferation before the periosteal graft is secured to the surface of the scaffold. The periosteal graft may be sutured to the scaffold. Preferably, the periosteal graft is sutured to the scaffold such that the cambium layer faces away from the defect (into the joint) when the composite is arranged in the defect.

The porous scaffold integrates with surrounding bone and the periosteal graft integrates with the scaffold when the composite is arranged in the defect. Typically, the scaffold and the periosteal graft occupy less than an entire volume of the defect when the composite is arranged in the defect, and a remaining volume of the defect is subsequently filled by periosteal-derived subchondral bone and neocartilage formation.

Figure 4:
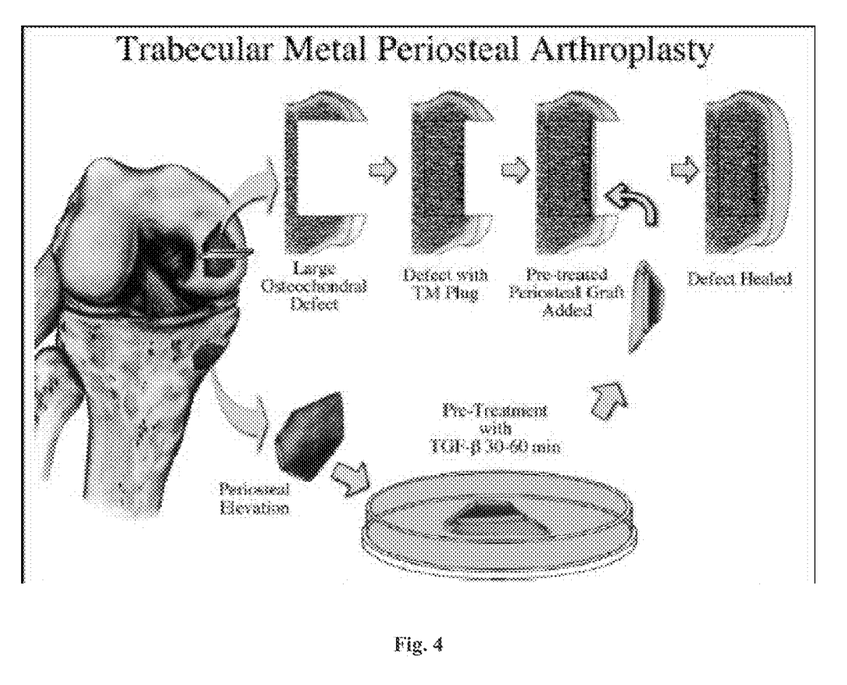
FIG. 4 is a schematic representation of one technique according to the invention for the repair of major osteochondral defects.

FIG. 4 shows a schematic representation of an example technique of "Trabecular Metal Periosteal Arthroplasty" for the repair of major osteochondral defects. In the schematic of FIG. 4, repair of a lesion on the medial femoral condyle is shown using one version of the present invention. Periosteum is harvested from the medial proximal tibia using a sharp periosteal elevator. The periosteal graft is incubated for 30-60 minutes in a sterile medium containing 100 ng/mL TGF-β to stimulate periosteal cell proliferation and neocartilage formation The defect is then debrided and filled with a trabecular metal (e.g., tantalum) plug so the top of the scaffold is below the level of the surrounding subchondral bone. The periosteal graft is then sutured to the scaffold with the cambium layer facing into the joint. The tantalum will integrate with the surrounding bone and the periosteal graft will integrate with the scaffold via tissue ingrowth. The remaining defect will then be filled by periosteal-derived subchondral bone and neocartilage formation.

The implications of the present invention can be great in terms of the number of patients affected and the quality of life for each of those patients. As several hundred thousands of total knee replacements for arthritis or other operations to treat articular defects in the knee are performed each year in United States, the method for cartilage regeneration could ultimately decrease the long-term costs of health care related to joint replacement and multiple revisions thereof. Most tissue-engineering techniques utilize in vitro culture expansion and seeding of cells onto a matrix. While this general approach may be feasible, it is expensive and technically challenging. The invention described herein does not require an in vitro culture expansion step. The periosteum does not undergo an in vitro cell culture expansion step. By eliminating the need for cell culture expansion facilities and expertise, the cost of this approach of the present invention should be considerably less, thereby making cartilage repair more globally accessible. Additionally, this concept may be applicable with other trabecular scaffolds than tantalum, or even with other cartilage-generating sources than periosteum.

Examples

The following Examples have been presented in order to further illustrate the invention and are not intended to limit the invention in any way.

Experimental Methods

1. Periosteal Harvesting

Using a dermal punch 3.5-mm in diameter and sharp subperiosteal elevation, explants of periosteum are harvested from the medial proximal tibiae from two-month-old New Zealand white rabbits. Immediately after surgical harvesting, the periosteal explants are placed in Dulbecco's Modified Eagle Media (DMEM), with penicillin/streptomycin and 1 mM proline at 4° C. for no more than 1.5 hours prior to placement into the defect or into culture wells.

2. Histology

Samples are embedded in methyl methacrylate and sectioned using an Exakt™ System and stained with safranin O/fast green.

3. Histological Analysis

A standardized cartilage yield assay was performed after six weeks of culture (see O'Driscoll et al., "A method for automated cartilage histomorphometry." *Tissue Eng.* 5:13-23, 1999). The control explants (Group IV, V and VI of FIG. 7) were weighed and embedded in paraffin, sectioned, and stained with safranin O/fast green. In addition, some of the explants from the tantalum groups (Groups I and II of FIG. 7) were also detached from the tantalum after 6 weeks of culture and processed as described below.

The simple histological-histochemical cartilage scoring system validated previously was used to analyze all the histological slides (see O'Driscoll et al., "Validation of a simple histological-histochemical cartilage scoring system." *Tissue Eng.* 7:313-320, 2001) The scoring system is shown in Table 1.

TABLE 1

The Simple Histological-Histochemical Cartilage Scoring System

| Score | Histological-Histochemical Findings Chondrocytes | Safranin O Staining |
|---|---|---|
| 0 | None (or almost none) | None (or almost none) |
| 1 | <50% | Slight |
| 2 | >50% | Moderate |
| 3 | All (or almost all) | Normal (or nearly normal) |

In samples that were attached to the tantalum piece, we evaluated the thickening of the new cartilage overgrowth from the tantalum using a new proposed qualitative score (see Table 2).

TABLE 2

Qualitative Score for Thickening of the Cartilage Grown Up Over the Tantalum

| Thickness of cartilage overgrowth | Qualitative Thickness Score |
|---|---|
| 0-1 mm. | 0 |
| 1-2 mm. | 1 |
| >2 mm. | 2 |

This thickness was also compared with their respective controls.

4. Collagen Typing

Quantitative collagen typing is performed by a previously published technique using an automated PhastSystem gel electrophoresis system (Pharmacia-LKG Biotechnology Group, Baie d'Urfe, Quebec, Canada) (see O'Driscoll et al., "A method for quantitative analysis of ratios of types I and II collagen in small samples of articular cartilage.". *Anal. Biochem.* 145:277-285, 1985). A 1-μL volume of sample, 8 μg/μL in sample buffer, is applied to and separated on 20% homogeneous SDS-PAGE Phast-Gels (Pharmacia-LKG Biotechnology Group, Baie d'Urfé, Québec, Canada). The gels are then scanned using an LKB laser densitometer (Pharmacia LKB Biotechnology Group), and the absorbance curves integrated with a computer software package (Gel-Scan, Pharmacia-LKB Biotechnology Group, Canada). Percent type II collagen is determined by calculating the ratio area under the α1 (II) CB10 peak to that under the α1 (II) CB11 peaks.

5. Mechanical Properties

Figure 7:
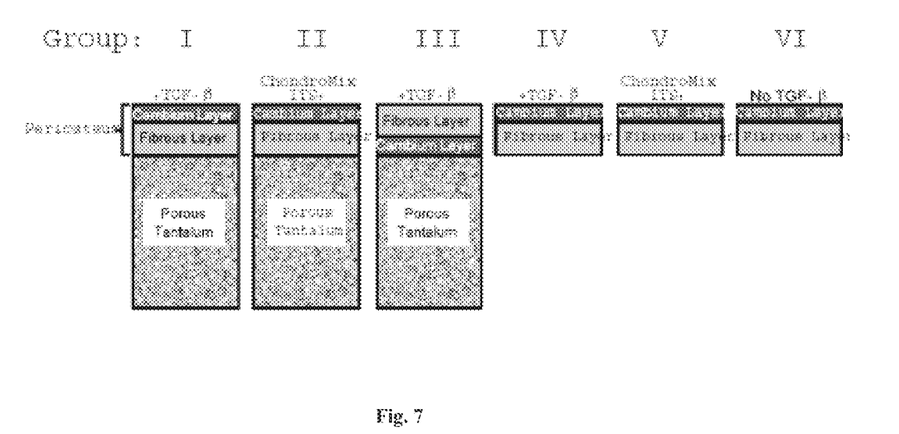
FIG. 7 shows the treatment groups of control explants and periosteum/tantalum composites that were cultured in vitro with or without additional supplements.
Figure 14:
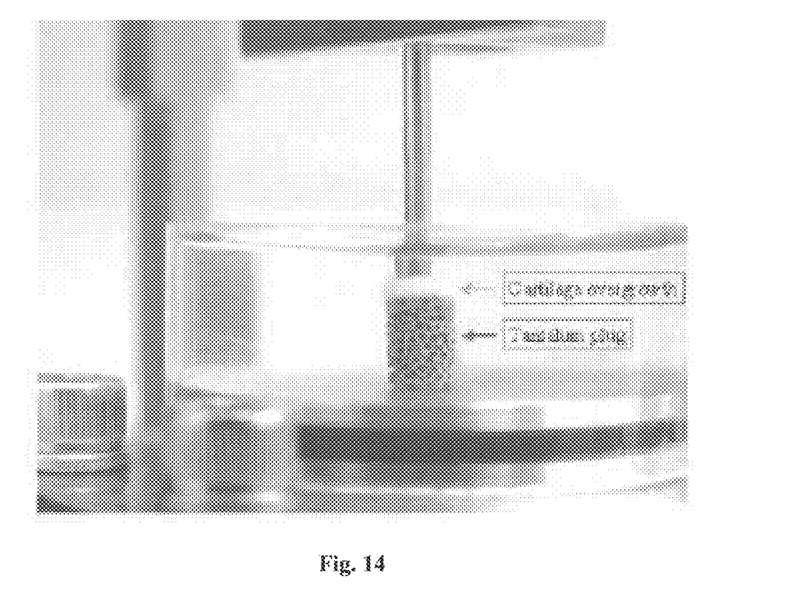
FIG. 14 shows a dynamic mechanical analyzer used to apply the loading in a cartilage indentation study performed on the periosteum/tantalum composites. In the indentation testing photograph, a six weeks cultured construct (tantalum/periosteum) is being tested by a A Dynamic Mechanical Analyzer machine.

A cartilage indentation study was performed on the periosteum/tantalum composites produced by attaching the periosteum to the tantalum with the cambium layer facing away from the porous tantalum and stimulated with TGF-β1 (Group I of FIG. 7, n=5). The mechanical properties of the composites were compared to normal osteochondral plugs (normal controls) obtained from 2 two-month old rabbits from a condylar area of the knee (n=3). Indentation testing was performed using a method similar to that described at Duda et al., "Mechanical quality of tissue engineered cartilage: results after 6 and 12 weeks in vivo", *J. Biomed. Mater. Res.* 53, 673-7, 2000. The specimen was placed unconstrained on a flat dish with the cartilage surface perpendicular to the 1.6 mm. cylindrical indenter. Loading was applied at a rate of 5N/minute to a maximum force of 5N (maximum applied stress=2.5 MPa). A Dynamic Mechanical Analyzer (TA Instruments, New Castle, Del.) was used to apply the loading (see FIG. 14). The 5N load limit compressed the cartilage beyond the toe region of the stress-strain curve. Since the bone/tantalum is much stiffer than the cartilage all deformation was assumed to be occurring in the cartilage. During testing the specimens were immersed in saline. Applied stress was calculated by dividing the applied force by the area of the indenter. Strain was defined as the indentation displacement divided by the original cartilage thickness. Elastic modulus was calculated as the slope of the linear region of the stress-strain curve between 0 and 0.5 MPa applied stress and less than 20% strain.

6. Statistical Analysis

Data are analyzed by two-way ANalysis of VAriance (ANOVA). Significant main effects are further analyzed using post hoc testing such as the Student-Newman-Keuls procedure.

7. Data

We evaluated the feasibility of developing a biologic and prosthetic implant composite using a porous tantalum scaffold and the chondrogenic potential of periosteum in an established in vitro culture model.

Figure 6:
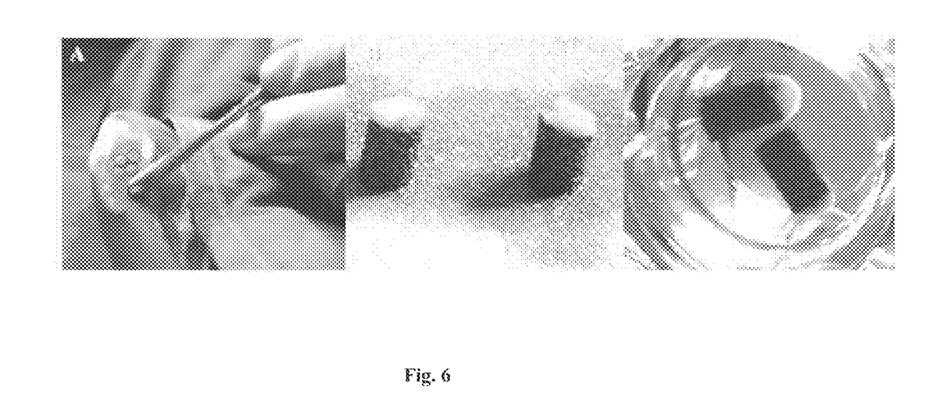
FIG. 6 includes photographs showing the development of periosteum/tantalum composites for in vitro testing.

Using a standard technique, periosteal explants (3 mm in diameter) were harvested from the medial proximal tibiae of 2 two-month-old New Zealand white rabbits (see FIG. 6A). The explants were then divided into six treatment groups as described below. Periosteum/tantalum composites were formed by attaching the explants onto porous tantalum cylinders (3 mm diameter×5 mm long) (see FIG. 6B). In initial experiments, the periosteal explants were carefully sutured to the tantalum. Subsequently, we discovered that use of a suture was not necessary for the in vitro experiments because the explants remained attached to the tantalum in a manner similar to hook and loop (e.g. Velcro™) fasteners after simply placing the explants onto the tantalum. Control explants and composites were cultured in vitro (see FIG. 6C)

with DMEM, 1% agarose, 10% fetal bovine serum with or without additional supplements as described below and summarized in FIG. 7. The explants and composites were supplemented either with TGF-β1 (10 ng/ml) for the first 2 days, or "ChondroMix ITS+" (10% FBS, 10 ng/ml TGF-β1, 5 µg/ml Growth Hormone (GH), 50 ng/ml basic Fibroblast Growth Factor (bFGF), and 3.3 µl/ml ITS+ (0.625 mg/ml insulin, 0.625 mg/ml transferrin, 0.625 µg/ml selenious acid, 0.125 mg/ml BSA and 0.535 mg/ml linoleic acid)) for the first 2 days followed by ITS+ only for the remainder of the culture period, or no additional supplements. In order to determine the effect of periosteal orientation on our construct, four explants were attached to the tantalum disks with the cambium layer facing down to the porous tantalum and cultured as described above with TGF-β1 (10 ng/ml) supplementation for the first 2 days. The cambium layer of the periosteum contains the chondrocyte precursor cells and is, therefore, the layer in which chondrogenesis originates. Positive control explants were cultured without tantalum and supplemented with TGF-β1 (10 ng/ml) or "ChondroMix ITS+". Negative control explants were cultured without tantalum or growth factor supplement.

The explants and composites were cultured for six weeks. The samples were then analyzed for tissue growth and integration, cartilage formation, collagen type II, or biomechanical properties (see Experimental Methods above for methods).

8. Results

A. Periosteal Growth

Figure 5:
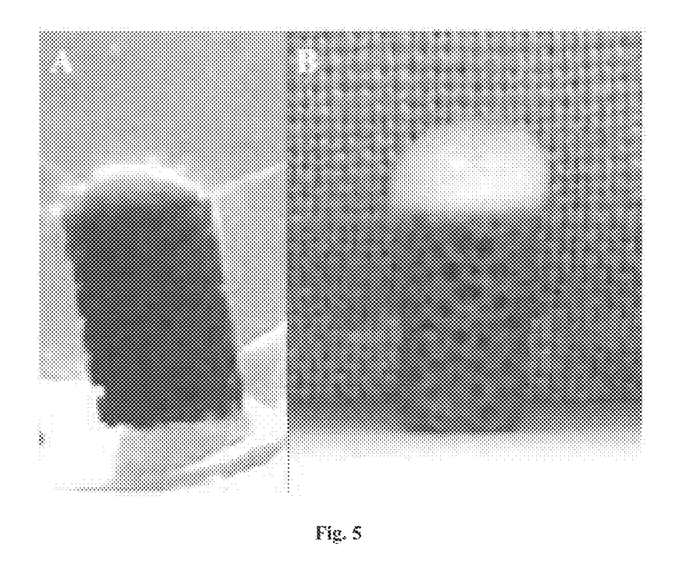
FIG. 5 includes photographs showing tissue outgrowth from periosteum/tantalum composites after six weeks of culture.
Figure 8:
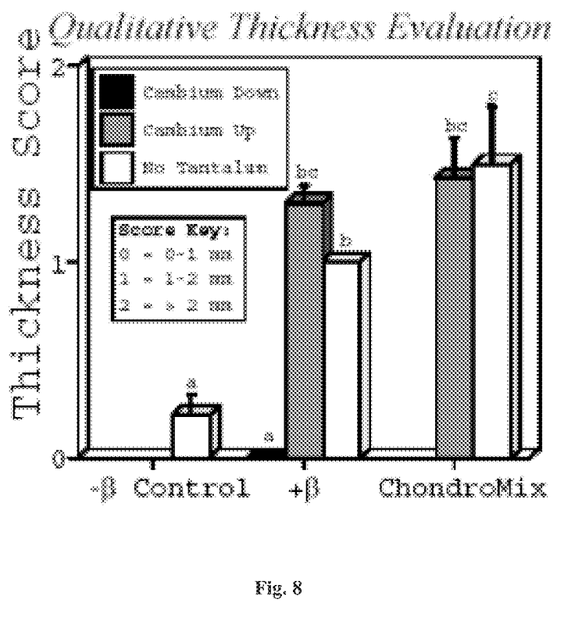
FIG. 8 is a graph showing a qualitative thickness evaluation of periosteum and periosteum/tantalum composites after six weeks of culture. Lower case letters indicate the results of post-hoc testing at $p<0.05$. Columns with letters in common are not statistically different from one another. The thickness of cartilage formed was not impeded by the presence of the tantalum.

Periosteum attaches to and grows out from porous tantalum. After six weeks of culture, the periosteal explants were well attached to the porous tantalum. Outgrowth of neocartilage was observed in the composites with the cambium layer of the periosteum facing away from the tantalum whereas no neocartilage outgrowth was observed in the composites with the cambium layer facing the tantalum (see FIG. 5A). As illustrated in FIG. 5, the overall thickness of the periosteal tissue over the tantalum was also significantly greater in the groups with cambium layer facing up compared to facing down. In constructs with the cambium layer facing up, the thickness of the new cartilage growth over the tantalum was also comparable to the respective controls grown in absence of tantalum (see FIG. 8). The best thickness score was observed in the tantalum/periosteal composites cultured with "ChondroMix ITS+" (>2 mm), while the least outgrowth of tissue was observed when the cambium layer was attached facing down towards the trabecular metal (see FIG. 8).

B. Histology

Figure 9:
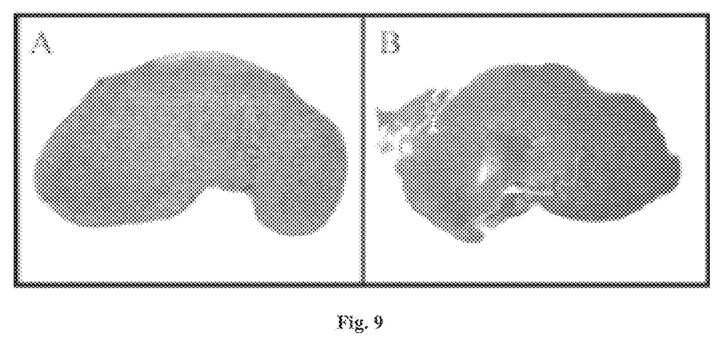
FIG. 9 includes photographs showing the typical histological appearance of periosteal explants with a score of 3 after six weeks of culture with and without tantalum.

Composites form neocartilage outgrowth and fibrous ingrowth. The nature of the tissue outgrowth was dependent on the orientation of the periosteum. Specifically, neocartilage outgrowth was only observed in composites containing periosteum with the cambium layer facing up away from the tantalum. Initial confirmation of cartilage production in the composites was achieved by removing the periosteal outgrowth from the composite after the six-week culture period and analyzing the tissue using standard safranin O/fast green histology techniques. As shown in FIG. 9, the cartilage yield obtained from the composites was comparable to the cartilage yield from control periosteal explants (explants cultured without tantalum). The Exakt™ System was then used to produce sections of the entire composites for analysis of tissue ingrowth and cartilage formation.

Figure 10:
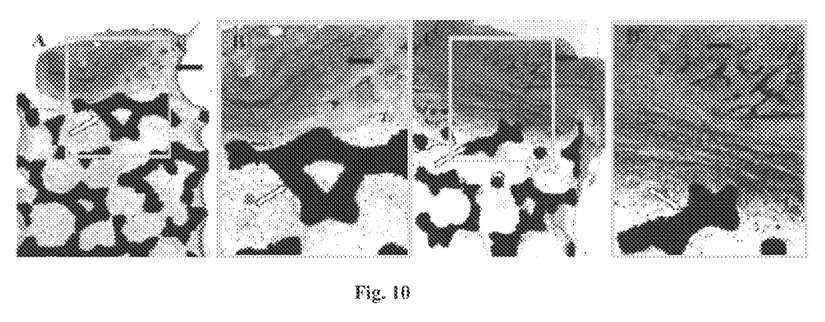
FIG. 10 includes photographs showing the histological examination of periosteum/tantalum composites. Examples are shown of composites after six weeks of culture in chondrogenic medium. The composites were embedded and sectioned using the Exakt™ System and stained using safranin O/fast green.
Figure 11:
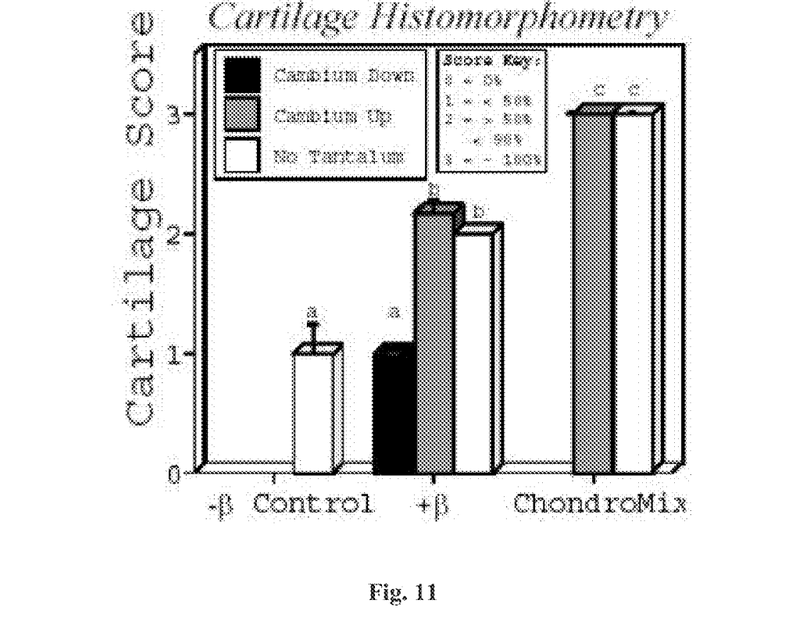
FIG. 11 is a graph showing a cartilage histomorphometric analysis of periosteum and periosteum/tantalum composites after six weeks of culture. Lower case letters indicate the results of post-hoc testing at $p<0.05$. Columns with letters in common are not statistically different from one another. Cartilage formation was not impeded by the presence of the tantalum.

As illustrated in FIG. 10, ingrowth of tissue was observed in all of the composites regardless of the orientation of the periosteum. The majority of the tissue ingrowth was fibrous in nature, however, some positive staining for cartilage was also observed within the tantalum. The nature of the tissue outgrowth was dependent on the orientation of the periosteum. Specifically, neocartilage outgrowth was only observed in composites containing periosteum with the cambium layer facing up away from the tantalum. FIG. 11 summarizes the cartilage histomorphometry scores for all of the treatment groups. The highest cartilage production was observed in the "ChondroMix ITS+" treated groups. No significant difference in cartilage production was observed between the composites with the cambium layer facing up away from the tantalum, and the positive controls (no tantalum) in either the TGF-β or the "ChondroMix ITS+" treated samples.

C. Collagen Type II

Figure 12:
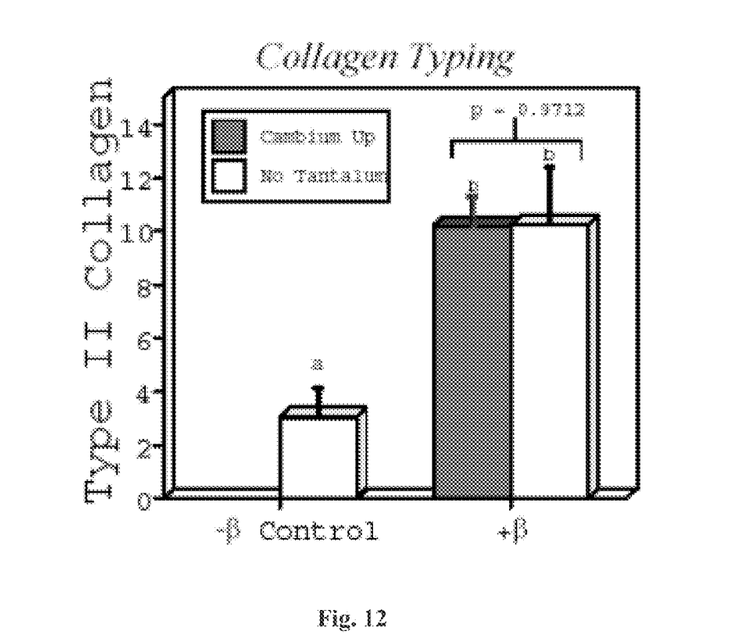
FIG. 12 is a graph showing a collagen typing analysis of periosteum and periosteum/tantalum composites after six weeks of culture. Lower case letters indicate the results of post-hoc testing at $p<0.05$. Columns with letters in common are not statistically different from one another. Type II collagen production was not impeded by the presence of the tantalum.

Periosteal type II collagen synthesis is maintained in composites. In order to further evaluate the matrix production in the periosteum/tantalum composites collagen typing analysis was performed. As shown in FIG. 12, no statistically significant difference in the relative amount of type II collagen with respect to type I was observed in explants treated with TGF-β1 either in presence or absence of tantalum (p=0.9). The relative amount of collagen type II produced in the TGF-β1 treated composites and positive control explants was significantly greater than in the negative control explants (no growth factor treatment).

D. Mechanical Properties

Figure 13:
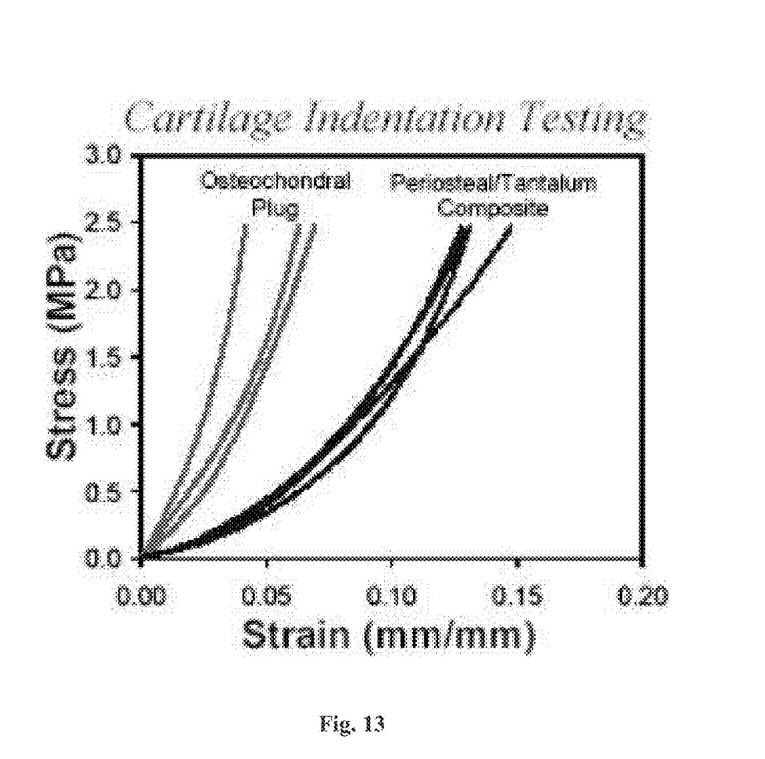
FIG. 13 is a graph showing a mechanical properties analysis of periosteum/tantalum composites compared to osteochondral plugs. Periosteal/tantalum composites were cultured for six weeks with 10 ng/mL TGF-β supplementation for the first two days. The composites had mechanical properties comparable to the osteochondral plug controls as can be seen by the similarly shaped curves.

Composites have mechanical proprieties similar to normal osteochondral tissue. We examined the mechanical properties of the periosteum/tantalum composites, using indentation analysis, and compared them to the properties of normal osteochondral plugs taken from the femoral condyles of rabbits. As shown in FIG. 13, the shape of the strain/stress curves produced from the tantalum/periosteal composites resembles the curve shape obtained with the normal osteochondral plugs. The tantalum/periosteal composite curve is displaced to the right, however, reflecting less stiffness than the normal osteochondral plug. It is important to note, however, that after 6 weeks of culture, the composites contain less mature cartilage (50% positive staining for cartilage) compared to mature cartilage in the normal osteochondral plug. In addition, the tantalum is only filled with fibrous tissue after culturing the composites for six weeks in vitro. Therefore, overall the composites used in this experiment are not developed to the stage expected after full integration into an osteochondral defect.

9. Discussion

We have developed a biosynthetic composite resembling an osteochondral plug using porous tantalum and periosteum. After 6 weeks of culture in chondrogenic media, the fibrous layer of the periosteum was strongly attached to the porous tantalum scaffold and the cambium layer when facing away from the tantalum created a hyaline-like cartilage tissue. When the cambium layer was facing up, the overall growth of the periosteal tissue was not significantly different than periosteal explants cultured in the absence of tantalum. Histological and biochemical analysis of the composites revealed that the quality of the cartilage produced in the explants was not negatively affected by the presence of the tantalum. In addition, the mechanical properties of the cultured tantalum/periosteal composites are similar to the natural osteochondral plugs, albeit less stiff at an initial stage of development. The stress-strain curves and elastic modulus of the periosteal tantalum composites have a clear tendency to improve as the percentage of cartilage is increased by the addition of chondrogenic factors to the culture medium. It is important to note that although the tissue outgrowth in the "ChondroMix" treated composites is 100% cartilage; it lacks the zonal organization observed in normal articular cartilage. It has been suggested that the zonal organization of chondrocytes and collagen matrix in mature articular cartilage is fundamental to the singular mechanical response of the tissue to stress. The results obtained in this study suggest that the three-dimensional organization of the cartilage may be responsible for almost 40% of the mechanical properties of mature articular cartilage.

The results of these experiments clearly demonstrate that under in vitro chondrogenic conditions, periosteum is compatible with the porous tantalum. The periosteal tissue integrated well with the tantalum by complete ingrowth of periosteal derived cells regardless of the orientation of the tissue. Thus, biological resurfacing of large osteochondral defects is feasible using a porous tantalum-autologous periosteal construct.

In summary, the results of these experiments clearly demonstrate that under in vitro chondrogenic conditions, periosteum is compatible with porous tantalum. The periosteal tissue integrated well with the tantalum by complete ingrowth of periosteal derived cells regardless of the orientation of the tissue. In addition, when the periosteum was attached to the tantalum with the cambium layer facing away from the tantalum, neocartilage formation was observed. When the cambium layer was facing up, the overall growth of the periosteal tissue was not significantly different than periosteal explants cultured in the absence of tantalum. Histological analysis of the composites revealed that the quality of the cartilage produced in the explants was not negatively affected by the presence of the tantalum. Based on collagen typing analysis, the matrix formation in the composites was also unaffected by the presence of tantalum. In addition, the mechanical properties of the cultured tantalum/periosteal composites were similar to the properties of a natural osteochondral plug, albeit less stiff at an initial stage of development.

Because periosteal growth and chondrogenesis is not hindered by the presence of the tantalum when the periosteum is stitched with the cambium layer facing away from the tantalum, biological resurfacing of large osteochondral defects may be feasible using a porous tantalum/autologous periosteal construct. In addition, the robust ingrowth of periosteal tissue may further enhance the healing of large osteochondral defects by enabling firm attachment and integration of the periosteal explant.

Thus, the invention provides a composite with the biochemical and mechanical properties of an autologous osteochondral graft with better integration properties and without the need for osteochondral graft harvesting.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A composite for the repair of osteochondral defects, the composite comprising:
   a biocompatible porous scaffold; and
   a cartilage-generating graft secured to a surface of the scaffold, wherein the cartilage generating graft is harvested periosteum,
   wherein the periosteum does not undergo an in vitro cell culture expansion step;
   wherein the periosteum is attached to the scaffold such that an inner layer of the periosteum faces away from the scaffold, wherein the inner layer is a cambium layer.

2. The composite of claim 1 wherein:
   the scaffold comprises a metallic material, and
   the scaffold has interior open spaces defined by an interconnecting network of channels.

3. The composite of claim 1 wherein:
   the scaffold comprises tantalum, and
   the scaffold has interior open spaces defined by an interconnecting network of channels.

4. The composite of claim 1 wherein:
   the periosteum is autologous.

* * * * *